United States Patent [19]
Beurrier

[11] Patent Number: 5,300,047
[45] Date of Patent: Apr. 5, 1994

[54] TROCAR CANNULA AND CATHETER

[76] Inventor: Henry R. Beurrier, 817 Old Chester Rd., Far Hills, Chester Township, Morris County, N.J. 07931

[21] Appl. No.: 952,685

[22] Filed: Sep. 29, 1992

[51] Int. Cl.$^5$ .................. A61M 25/00; A61M 5/14; A61M 1/00
[52] U.S. Cl. .................. 604/264; 604/256; 604/31; 137/487.5
[58] Field of Search .................. 604/31, 33, 34, 67, 604/98, 99, 100, 162, 165, 167, 169, 256, 268, 273, 274; 251/5, 61.1; 137/487.5

[56] References Cited

U.S. PATENT DOCUMENTS

| | | | |
|---|---|---|---|
| 2,598,207 | 5/1952 | Bailey et al. | 251/61.1 |
| 3,397,860 | 8/1968 | Bushmeyer | 251/61.1 |
| 4,079,738 | 3/1978 | Dunn et al. | 604/165 |
| 4,275,793 | 6/1981 | Schivley, Jr. et al. | 137/487.5 |
| 4,364,392 | 12/1982 | Strother et al. | 604/98 |
| 4,502,482 | 3/1985 | DeLuccia et al. | 604/165 X |
| 4,535,773 | 8/1985 | Yoon | 604/169 X |
| 4,610,671 | 9/1986 | Luther | 604/264 X |
| 4,686,962 | 8/1987 | Haber | 604/274 X |
| 4,787,408 | 11/1988 | Twerdochlib | 251/61.1 |
| 4,932,959 | 6/1990 | Horzewski et al. | 604/96 X |
| 5,104,389 | 4/1992 | Deem et al. | 604/167 X |
| 5,161,773 | 11/1992 | Tower | 251/5 |
| 5,186,431 | 2/1993 | Tamari | 604/34 X |
| 5,190,068 | 3/1993 | Philbin | 137/487.5 X |

Primary Examiner—C. Fred Rosenbaum
Assistant Examiner—Frank Wilkens
Attorney, Agent, or Firm—Herbert M. Shapiro

[57] ABSTRACT

A TROCAR catheter assembly employs a regulated gas flow between a catheter and the inner wall of a cannula sleeve in which the catheter moves. Annular grooves are formed in the wall of the sleeve and the grooves are connected to a source of gas which produces a pressure differential which causes gas to flow in a manner to control passage of gas to or from a body cavity in which the sleeve is inserted. In one embodiment, one of the annular grooves is connected to a bladder which is inflated to seal the entire opening defined by the inner wall of the sleeve when the catheter is absent.

11 Claims, 6 Drawing Sheets

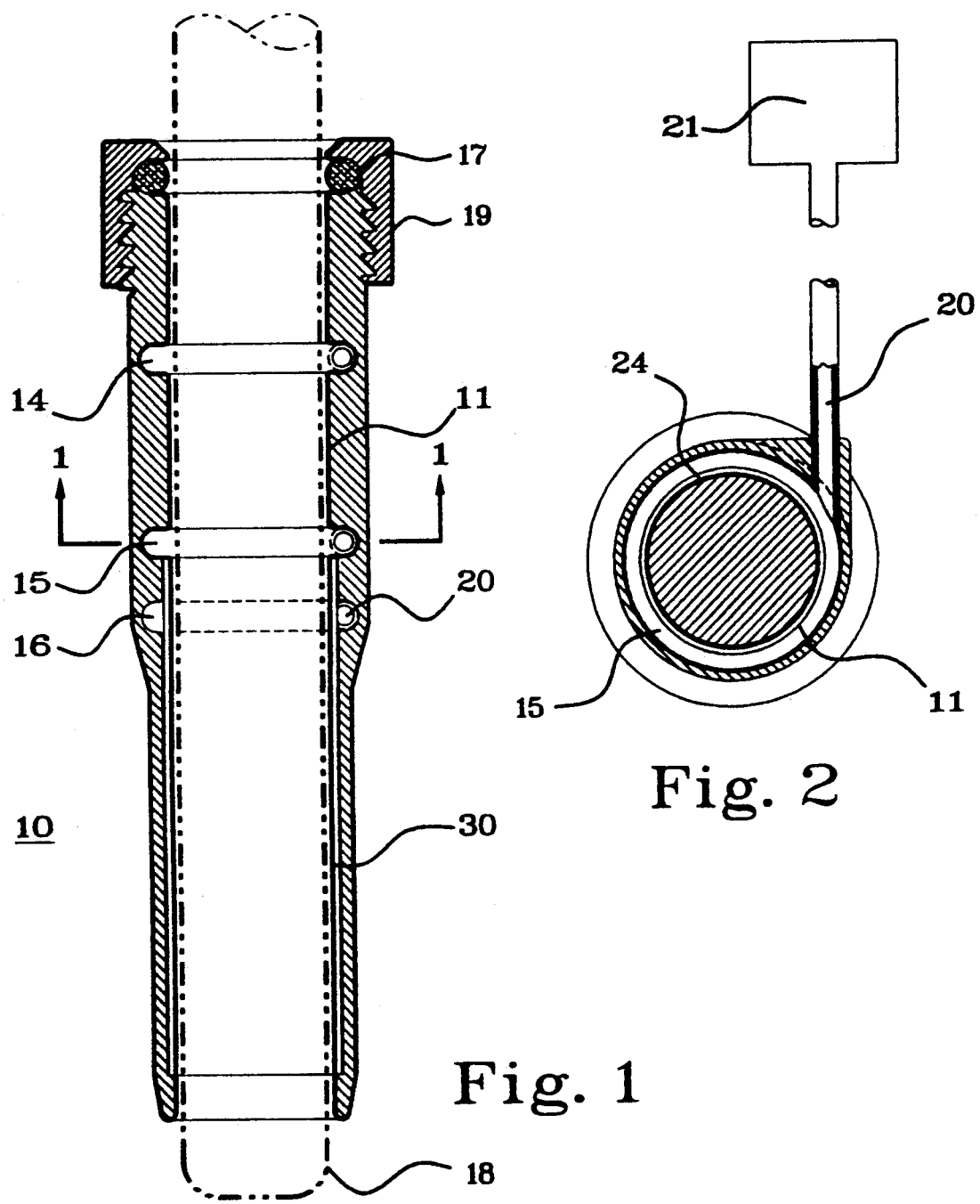

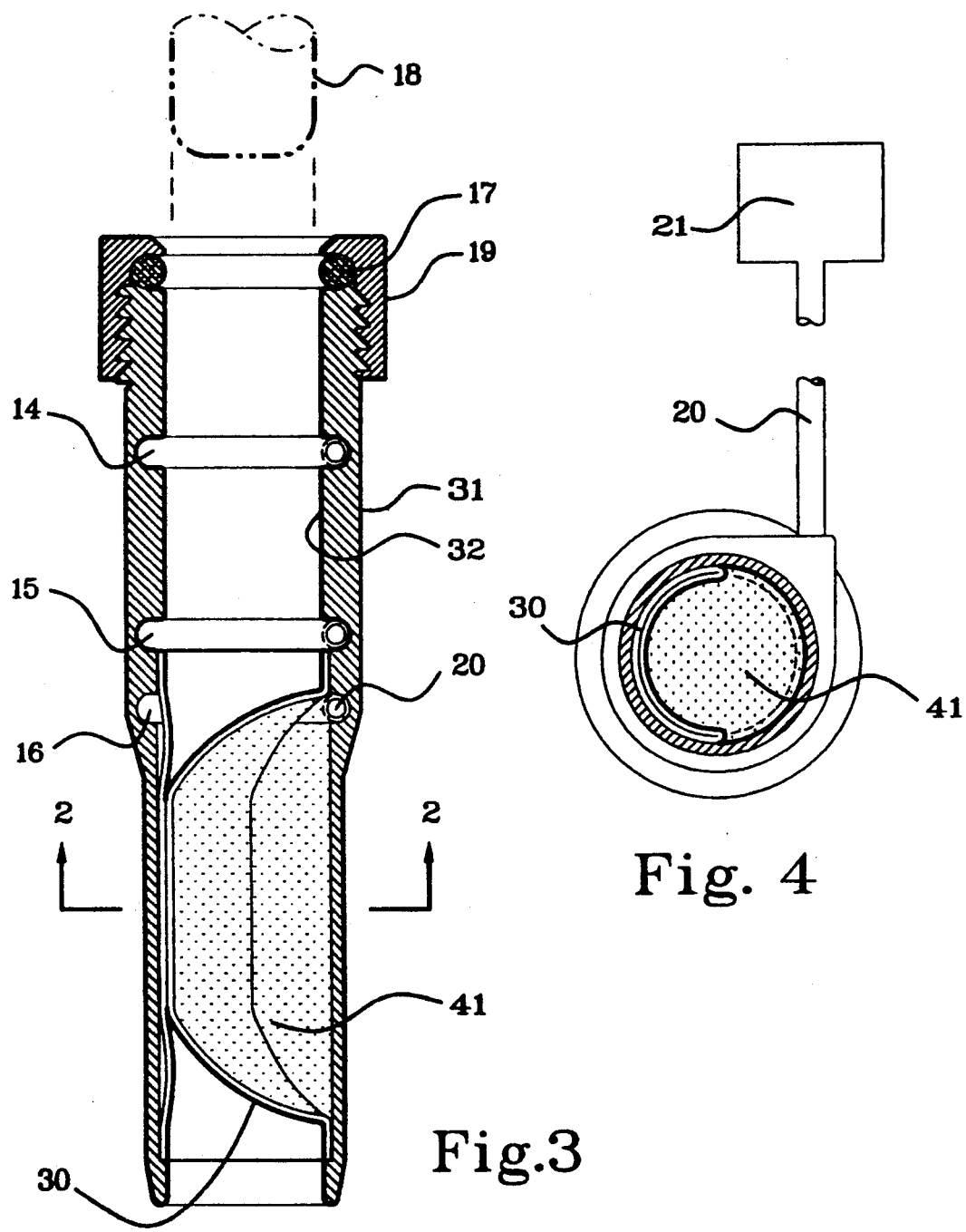

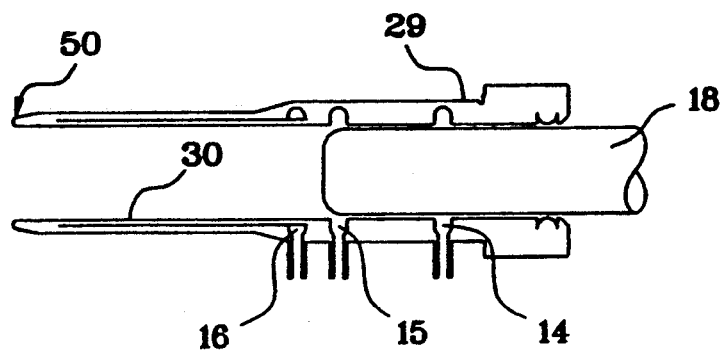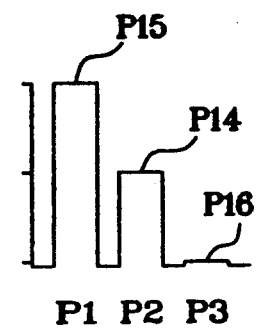
Fig. 5     Fig. 5A
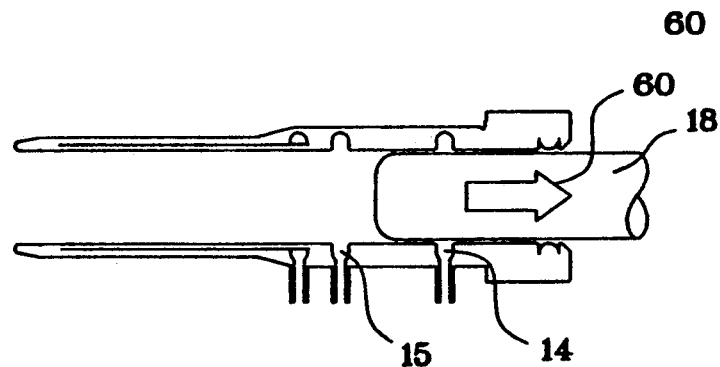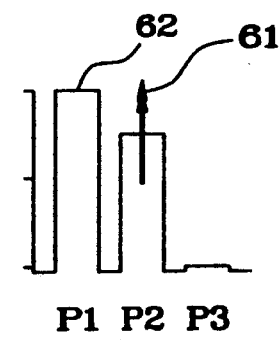
Fig. 6     Fig. 6A

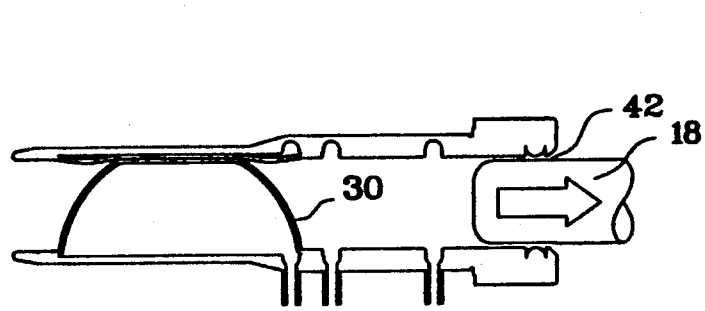
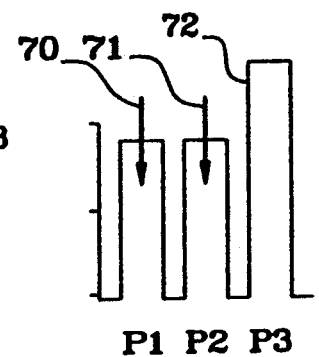
Fig. 7            Fig. 7A
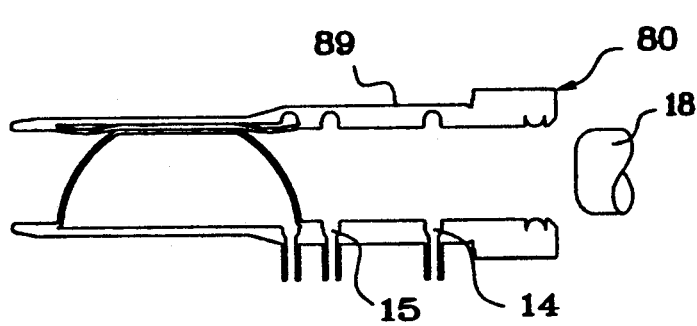
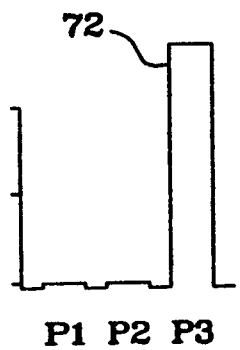
Fig. 8            Fig. 8A
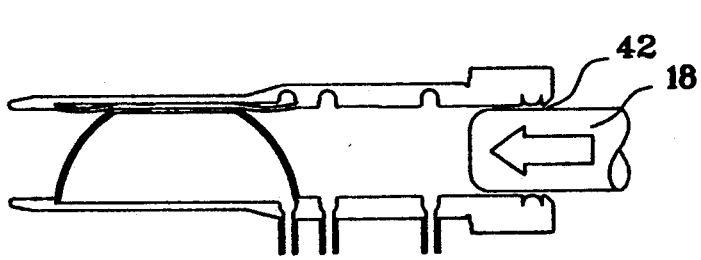
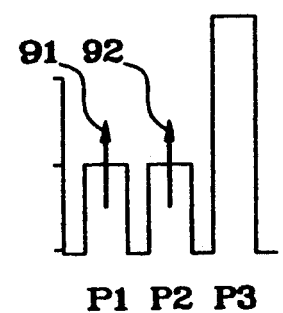
Fig. 9            Fig. 9A

TROCAR CANNULA AND CATHETER

FIELD OF THE INVENTION

This invention relates to cannulas for medical usage and more particularly, to trocar cannulas and catheter assemblies.

BACKGROUND OF THE INVENTION

A trocar catheter is generally employed to penetrate an abdominal wall of a patient and can include a central stylet for the actual penetration and a surrounding tube through which gases and/or fluids may be injected or removed into or exhausted from the abdomen of the patient Frequently, also a protective tube or cannula is used to encompass the entire device to be inserted into the abdomen once penetration has occurred. Additionally various types of catheters and surgical instruments are manipulated through cannulas in endoscopic surgery.

A significant problem with catheters and surgical instruments, which have concentric, axial displaceable components, is to provide a seal between the components yet permit free axial displacement. A common solution to this problem is to provide some form of wiping seal or an inflatable collar which is expanded to fill the gap between such components. U.S. Pat. No. 4,932,959, issued Jun. 12, 1990, discloses an inflatable collar to this end used to release or secure a guide wire within a catheter. Also, U.S. Pat. No. 5,085,636 issued Feb. 4, 1992, discloses a balloon which is operative as an inflation and deflation valve to provide a fluid tight seal around a guide wire. In each instance, air pressure inflates an inflatable member which expands to occupy a space between components of the instrument. Such a mechanism is expensive, occupies considerable space, is not entirely reliable, and more importantly generates mechanical drag restricting free manipulation of the catheter.

BRIEF DESCRIPTION OF AN ILLUSTRATED EMBODIMENT OF THIS INVENTION

In accordance with the principle of this invention, a trocar cannula comprises a sleeve which has an inner wall into which a plurality of annular grooves are formed. A catheter is introduced into the sleeve and is designed to fit with a minimal uniform clearance between the catheter and the inner wall. Pressure regulated gas is continually introduced to a first annular groove at a pressure equal to the pressure of the abdominal cavity into which the sleeve is installed. In this manner essentially all gas escaping the cannula/catheter assembly is supplied by or replaced by gas supplied through the first annular groove, thus maintaining desired pressure in the abdominal cavity.

A second annular groove advantageously interposed between the first groove and the proximal (outside) end, is connected by tubulation to a gas pressure determining means, that is used to control, through a third annular groove, an inflatable collar at the distal end of the cannula, in order to seal off the abdominal cavity against atmospheric ambient, when the catheter is withdrawn.

With the catheter installed the pressure at the proximal (second) groove will equilibrate at a value between the pressure in the abdominal cavity and ambient atmospheric pressure, consistent with the location of the proximal annular groove and uniformity of the clearance between the catheter and the inner wall of the sleeve. As the catheter is removed, the pressure in the proximal annular groove is caused to increase toward that of the pressure at the first annular groove. When these two pressures are about equal, the collar is caused to inflate, effectively sealing off the abdominal cavity. Reinserting the catheter reverses the process by venting the collar to atmosphere, thus opening the cannula.

To reduce waste and distraction in the operating room, gas flow to the first groove is limited to a level slightly above that which is required to maintain abdominal pressure with the catheter in place.

Should the incision in the abdominal wall for the cannula be made manually or by some other means not directly requiring the use of the cannula, a catheter is provided to reduce additional trauma to the patient when the cannula is installed. In order to be gas tight, the incision is stretched open by the cannula when it is installed so that the incision fits snugly about the outside wall of the cannula. Prior to installing the cannula in the abdominal wall, the catheter is inserted and clamped in the cannula which has an expandable feature, that when compressed, guides the edges of the incision over the lip at the distal end of the cannula. Decompressing the expandable feature then allows the removal of the catheter, leaving the cannula in place.

BRIEF DESCRIPTION OF THE DRAWINGS

FIGS. 1 and 2 are orthogonal cross sectional views of a trocar cannula catheter assembly in accordance with this invention;

FIGS. 3 and 4 are orthogonal cross sectional views of a trocar catheter assembly having the collar inflated, in accordance with the principles of this invention;

FIGS. 5 through 9 and 5A through 9A are schematic representations of a multigroove trocar catheter assembly of FIGS. 1 through 4 along with associated pressure representations for different positions of a catheter within and without the sleeve of the assembly;

FIG. 10 is a schematic representation of the gas control and supply means for connection to the catheter assembly of FIGS. 1 through 4) and FIGS. 12 and 13 are cross sectional view of a catheter for use with the assemblies of FIGS. 1 through 4.

DETAILED DESCRIPTION OF ILLUSTRATIVE EMBODIMENTS OF THE INVENTION

Figure 10:
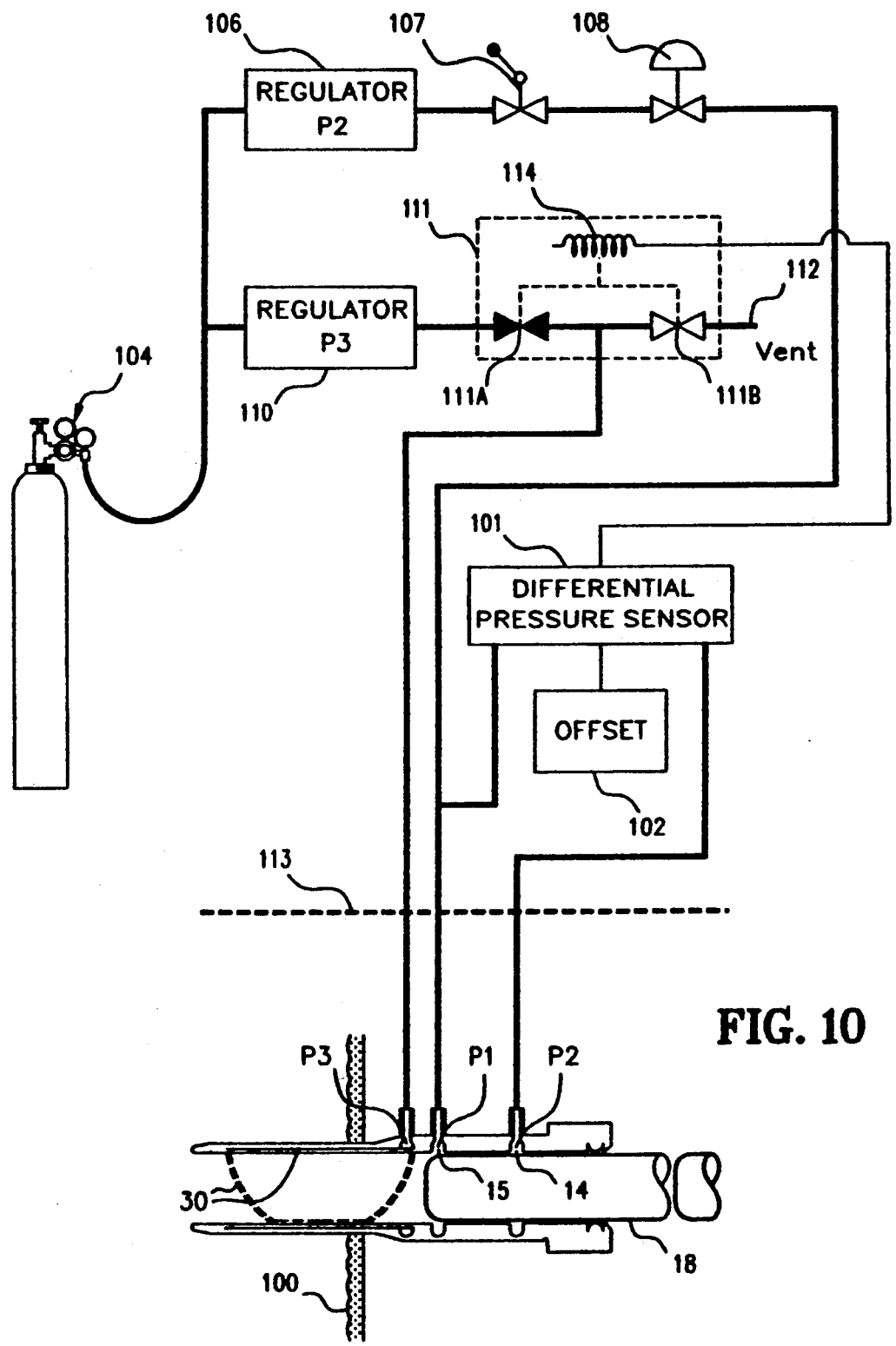

FIG. 1 shows a trocar cannula and catheter assembly 10 in accordance with the principles of this invention. The assembly includes a sleeve which has an inner wall 11 with three spaced-apart annular grooves 14 through 16. Grooves 14, 15 and 16 are formed as an annular indentation in the wall of the sleeve, having adequate volume to equalize gas pressure within their confines. Grooves 14 and 15 are open to the cylindrical space defined by the inner wall 11. Groove 16 is open to the enclosed volume of the inflatable collar bladder 30.

An optional sealing gasket, designated 17 in FIG. 1, extrudes against a catheter 18, when threaded ring 19 is tightened.

FIG. 2 is a cross section view of the assembly, taken at section 1—1 in FIG. 1. Annular groove 15 is connected through a tube to a pressure regulated and flow limited source of gas. The tube and gas source are designated 20 and 21 in FIG. 2. A catheter 18 is represented in FIG. 1 by broken lines which outline the shape of a catheter. The space between the catheter and the wall 11 of the sleeve is designated 24 in FIG. 2 and is typical of the minimum space between the uninflated collar 30 and the catheter of FIG. 1. The enlarged space at annular groove 15 is typical of that found in grooves 14 and 16.

FIGS. 3 and 4 show the trocar catheter assembly 10 of FIGS. 1 and 2, having the catheter 18 withdrawn and having collar/bladder 30 pressurized by gas introduced through tubulation 20 and annular groove 16 at a pressure about one and one half times the design pressure in the abdominal cavity. The collar/bladder 30 is shown in the inflated state, having extended entirely across the cylindrical space defined by the inner wall of the sleeve, thus sealing off the abdominal cavity. FIG. 4 is a cross section view, taken at section 2—2 in FIG. 3. Tube 37 connects annular groove 16 to the gas pressurizing and venting means.

The volume of inflation gas is designated 41 in FIGS. 3 and 4.

It should be noted that the collar/bladder needs only to be adhered and sealed at its ends to the inside surface of the sleeve at the annular surfaces located between the inner diameter of the cannula and the outer diameter of the bladder FIGS. 5 and 5A through 9 and 9A represent different phases of operation of the trocar catheter assembly of FIGS. 1 through 4 for different positions of the catheter, as well as the associated pressures, P1, P2 and P3, at annular grooves 14, 15 and 16. FIG. 5, for example, shows assembly 10 of FIG. 1 with the catheter 18 in a position corresponding to annular grooves 14 and 15 as shown. The distal end (50) of the sleeve is shown to the left, as viewed, and the inflatable bladder, 30, is shown near that end. As can be seen from the figure, catheter 18 can be advanced within the sleeve unobstructed by the bladder. In the position shown for the catheter in FIG. 5, the pressure, P1, at groove 15 is high, equalling the pressure in the abdominal cavity, as indicated by curve P15 in FIG. 5A and pressure P2 at groove 14, has equilibrated between pressure P1 and atmospheric pressure, as indicated by curve P14 in FIG. 5A. The pressure, P3, behind the bladder at groove 16 is essentially zero, as indicated by curve P16.

As the catheter is withdrawn, as indicated by arrow 60 of FIG. 6, the pressure, P2, in groove 14 rises as indicated by arrow 61 in FIG. 6A. pressure, P1, in groove 15 remains constant as indicated by 62.

FIG. 7 shows the effect of withdrawing catheter 18. The gas flow due to the flow restriction, loses ground against the increased leakage through the decreasing length of leak path 42. This results in the dropping of pressures, P1 and P2, as indicated by arrows 70 and 71. More importantly the pressures, P1 and P2, are about equal, Which causes the control circuitry to automatically inflate bladder 30, as evidenced by the extended bladder and high value of pressure, P3, indicated by curve 72 in FIG. 7A.

FIG. 8 shows catheter 18 removed from to proximal end 80 of the cannula (89). At this juncture in the operation, the pressures at grooves 15 and 14 are minimal and equal and the high pressure behind the bladder is continued high, as shown by curve 72 in FIG. 8A.

FIG. 9 shows the catheter having advanced beyond the position shown in FIG. 7. Corresponding pressures. P1 and P2, are shown in FIG. 9A, increasing as the gas leak path 42 is lengthened and still equal as indicated by curves 91 and 92, FIG. 9A.

When the catheter reaches a point approximating that shown in FIG. 5, the relative magnitudes of pressures P1 and P2 will equalize. This causes the circuit logic to automatically reverse the state of solenoid valve 111, (see FIG. 10) vent bladder 30 to the atmosphere and to allow the bladder to collapse, thus allowing free passage and manipulation of the catheter.

By arranging the circuit logic to switch the bladder pressure high whenever pressure P1 is higher than pressure P2, and further by applying a small positive pressure offset to the P2 detector, the condition when P1 is near equal to P2 is assured to be interpreted by the logic as that required to inflate the bladder, without imposing difficult tolerances on the pressure sensing means and/or requiring complex logic.

Threaded ring 19 and gasket 17, shown in FIGS. 1 and 3, provide a convenient means to clamp the catheter to the sleeve with minimal manual effort and operates in conjunction with the automatic control of the collar/bladder. Screwing in the threaded ring squeezes the elastomer gasket so that it extrudes against the catheter. This only needs to be done just enough to block the flow of gas through the gap between the catheter and cannula. Pressures P1 and P2 will then equalize, which will in turn cause the collar/bladder to automatically inflate, thus effectively clamping the catheter.

FIG. 10 is a schematic representation of the gas control and supply means for connection to the catheter assembly of FIGS. 1 through 4. The apparatus and its operation are shown in the context of an assembly with a catheter partially in the cannula and with the cannula in position in the cavity wall as indicated at 100. Annular grooves 14 and 15 are shown connected through tubing to the inputs of differential pressure sensor 101 to measure pressures P1 and P2. Another input to pressure sensor 101 is a mechanical or electrical offset means 102 to slightly bias P2 high, so as to simplify logic and ease tolerance on components.

Pressure regulated gas of a suitable medical grade is supplied by source 104 Source 104 is connected to a first pressure regulator 106 to supply pressure P1 to annular groove 15 through (manual) shut off valve 107 and flow restricting metering valve 108. The restricting means could be a needle valve or a capillary, both common in medical practice. The restricting means is set to limit the maximum delivery rate to the cannula to a level just above that required to maintain desired pressure P1, against the maximum design leakage between the inner wall of the cannula and the installed catheter.

A second regulator 110, connected to source gas 104, outputs gas at pressure, P3, on the order of one and one half times that of pressure, P1, maintained in the abdominal cavity. Solenoid valve assembly 111 connects collar/bladder 30 through normally closed valve 111A to regulator 110 output and alternately through normally open valve 111B to vent port 112. Valves 111A and 111B are operated by solenoid winding 114.

When the catheter is withdrawn, the differential pressure detector determines that pressure P2 is equal to or greater than pressure P1 and solenoid 114 is energized. Valve 111B is then transferred from its normally open state to the closed state and valve 111A is transferred from the normally closed state to the open state. The collar/bladder is thus transferred from the vented collapsed state, against the inner wall of the sleeve to the distended state, sealing off the abdominal cavity from ambient atmospheric pressure.

It is intended that only the cannula and the tubing below the broken line 113 in FIG. 10, be subjected to contamination by the patient and therefore disposable.

The catheter, depending on its nature, would be sterilized, recycled or disposed of.

Figure 11:
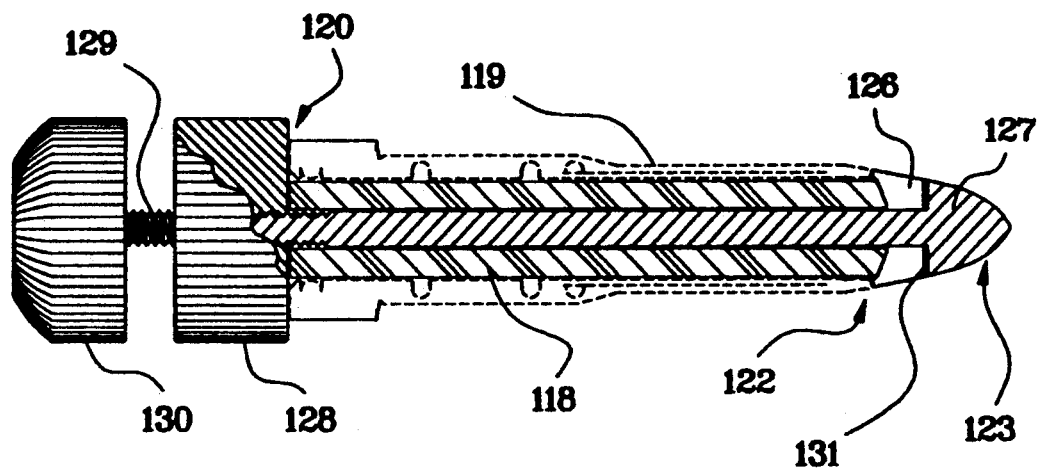

FIG. 11 is a partially cross sectioned view showing a catheter 118 inserted in the cannula of FIG. 1. The cannulla 119 is shown with broken lines for reference. Specifically FIG. 11 shows the catheter body having a generally cylindrical shape with a diameter to fit within the cannula. The catheter has a proximal end 120 and a distal end 122. The distal end is equipped with a tip assembly 123 having a controllably adjustable shape and shown in the relaxed state in FIG. 12. The adjustment of the tip is controlled by compressing the elastic member 126 between the tip 127 and the body of the catheter at the distal end, by tightening knurled thumb nut 128 against catheter body on threaded draw rod 129. Knob 130, affixed to the proximal end of draw rod 129, can be used to prevent the draw rod from turning when the knurled nut is operated. The elastic member 126 advantageously includes a bonded nonelastic mesh 131 or washer to prevent the lower distal end of the elastic member from expanding radially. Alternately member 126 could be bonded to tip 127.

Figure 12:
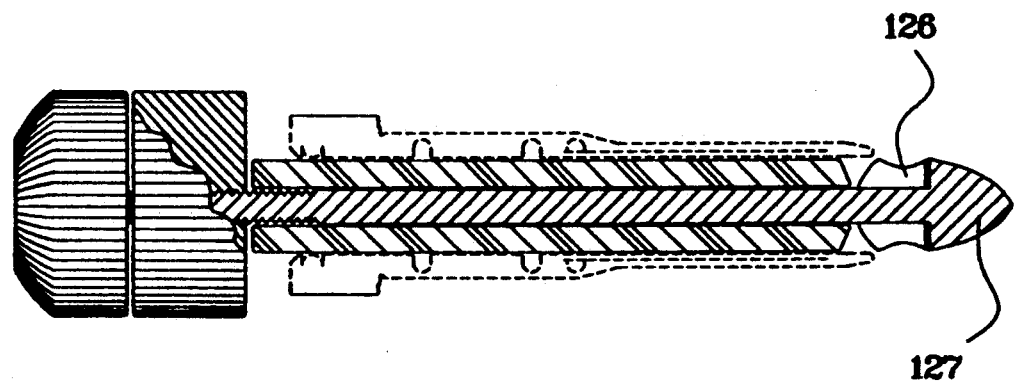

FIG. 11 shows the distal end of catheter in the extruded state, having the elastic member 126 extended to a smooth shape flush with the outside of the distal end of the cannula. FIG. 12 shows elastic member 126 in the relaxed state.

What is claimed is:

1. A catheter assembly comprising a sleeve having an inner and an outer surface, said sleeve having at least first and second annular grooves formed in said wall and being open to said inner surface and means connected to said grooves for providing a pressure differential therebetween wherein said means comprises a tube to each of said grooves and said tubes are connected to a source of gas.

2. A catheter assembly comprising a sleeve having an inner and an outer surface, said sleeve having at least first and second annular grooves formed in said wall and being open to said inner surface and including a tube connected to each of said grooves for providing a pressure differential therebetween.

3. A catheter assembly as set forth in claim 2 also including an inflatable bladder, said assembly having a proximal and a distal end, said bladder being located near said distal end, said assembly including means responsive to the absence of a pressure differential between said first and second grooves for inflating said bladder.

4. A catheter assembly as set forth in claim 3 also including a third groove and means connected to said third groove for providing gas to said bladder responsive to absence of pressure differential between said first and second annular groove.

5. A catheter assembly as set forth in claim 4 wherein said means responsive includes a third annular groove in said wall, said third groove being open to said inner surface and communicating with said bladder and a tube for connection to a supply of gas.

6. A catheter assembly as set forth in claim 2 also including a catheter closely fitting within said inner wall of said sleeve and being movable along the axis of said sleeve.

7. A catheter assembly as set forth in claim 6 wherein said catheter has a proximal and a distal end, said catheter including a tip assembly at said distal end, said tip assembly being adjustable between first and second configurations, said first configuration being of a geometry to permit movement of said catheter along said axis of said sleeve, said second configuration being of a geometry to conform to the distal end of said sleeve for providing a smooth distal end for the assembly.

8. A catheter assembly as set forth in claim 7 including control means at said proximal end of said assembly and means communicating between said control means and said tip assembly for adjusting the configuration of said tip assembly.

9. A catheter assembly as set forth in claim 3 also including a catheter closely fitting within said inner wall of said sleeve and being movable along the axis of said sleeve.

10. A catheter assembly as set forth in claim 9 wherein said catheter has a proximal and a distal end, said catheter including a tip assembly at said distal end, said tip assembly being adjustable between first and second configurations, said first configuration being of a geometry to permit movement of said catheter along said axis of said sleeve, said second configuration being of a geometry to conform to the distal end of said sleeve for providing a smooth distal end for the assembly.

11. A catheter assembly as set forth in claim 10 including control means at said proximal end of said assembly and means communicating between said control means and said tip assembly for adjusting the configuration of said tip assembly.

* * * * *